(12) United States Patent
Javitt

(10) Patent No.: US 9,486,453 B2
(45) Date of Patent: Nov. 8, 2016

(54) COMPOSITION AND METHOD FOR TREATMENT OF DEPRESSION AND PSYCHOSIS IN HUMANS

(71) Applicant: Glytech, LLC, Ft. Lee, NJ (US)

(72) Inventor: Daniel C. Javitt, Bardonia, NY (US)

(73) Assignee: Glytech LLC, Ft. Lee, NJ (US)

( * ) Notice: Subject to any disclaimer, the term of this patent is extended or adjusted under 35 U.S.C. 154(b) by 0 days.

(21) Appl. No.: 14/844,021

(22) Filed: Sep. 3, 2015

(65) Prior Publication Data
US 2015/0374684 A1 Dec. 31, 2015

Related U.S. Application Data

(62) Division of application No. 13/936,198, filed on Jul. 7, 2013.

(60) Provisional application No. 61/741,114, filed on Jul. 12, 2012, provisional application No. 61/741,115, filed on Jul. 12, 2012.

(51) Int. Cl.

| | | |
|---|---|---|
| *A01N 43/00* | (2006.01) |
| *A61K 31/553* | (2006.01) |
| *A61K 31/554* | (2006.01) |
| *A61K 31/496* | (2006.01) |
| *A61K 31/42* | (2006.01) |
| *A61K 31/06* | (2006.01) |
| *A61K 31/381* | (2006.01) |
| *A61K 31/55* | (2006.01) |
| *A61K 31/138* | (2006.01) |
| *A61K 45/06* | (2006.01) |
| *A61K 31/431* | (2006.01) |
| *A61K 31/4525* | (2006.01) |
| *A61K 31/519* | (2006.01) |
| *A61K 31/551* | (2006.01) |
| *A61K 31/135* | (2006.01) |

(52) U.S. Cl.
CPC ............ *A61K 31/496* (2013.01); *A61K 31/06* (2013.01); *A61K 31/135* (2013.01); *A61K 31/138* (2013.01); *A61K 31/381* (2013.01); *A61K 31/42* (2013.01); *A61K 31/431* (2013.01); *A61K 31/4525* (2013.01); *A61K 31/519* (2013.01); *A61K 31/55* (2013.01); *A61K 31/551* (2013.01); *A61K 31/553* (2013.01); *A61K 31/554* (2013.01); *A61K 45/06* (2013.01)

(58) Field of Classification Search
None
See application file for complete search history.

(56) References Cited

U.S. PATENT DOCUMENTS

| 6,228,875 B1 | 5/2001 | Tsai et al. |
| 2006/0204486 A1 | 9/2006 | Pyke et al. |
| 2008/0194631 A1 | 8/2008 | Trovero et al. |
| 2008/0194698 A1 | 8/2008 | Hermanussen et al. |
| 2010/0216805 A1* | 8/2010 | Barlow .............. A61K 31/12 514/249 |
| 2011/0207776 A1 | 8/2011 | Buntinx |
| 2011/0237602 A1* | 9/2011 | Meltzer ............. A61K 31/496 514/254.04 |
| 2011/0306586 A1 | 12/2011 | Khan |
| 2012/0041026 A1 | 2/2012 | Waizumi |

FOREIGN PATENT DOCUMENTS

| KR | 2007 0017136 A | 2/2007 |
| WO | WO 2005/000216 A2 | 1/2005 |
| WO | WO 2005/065308 A2 | 7/2005 |
| WO | WO 2005/079756 | 9/2005 |
| WO | WO 2011044089 | 4/2011 |
| WO | WO 2012/104852 A1 | 8/2012 |
| WO | WO2013138322 | 9/2013 |

OTHER PUBLICATIONS

Fenton, "Depression, Suicide and Suicide Prevention in Schizophrenia," American Foundation for Suicide Prevention Education section, http://www.afsp.org/education/fenton.htm (date accessed—Dec. 3, 2015).*
Jamison, "Suicide and bipolar disorder," J Clin Psychiatry. 2000;61 Suppl 9:47-51.*
Rogoz, Z. et al. "Synergistic effect of uncompetitive NMDA receptor antagonists and antidepressant drugs in the forced swimming test in rats" Neuropharmacology, Pergamon Press, Oxford, GB, 42(8): 1024-1030, XP002288820 (Jun. 2002).
Heresco-Levy, U. et al. "Controlled trial of d-cycloserine adjuvant therapy for treatment-resistant major depressive disorder" Journal of Affective Disorders, Elsevier Biochemical Press, Amsterdam, NL, 93(1-3): 239-243, XP024997304 (Jul. 2006).
Crane, G.E. "Cycloserine as an antidepressant agent" American journal of Psychiatry, American Psychiatric Publishing, Inc., US, 115(11): 1025-1026, XP009158563 (May 1, 1959).
Ceglia et al., "The 5-HT2A receptor antagonist M100,907 prevents extracellular glutamate rising in response to NMDA receptor blockade in the mPFC," Journal of Neurochemistry. 2004, 91, 189-199.
Mony et al., "Identification of a novel NR2B-selective NMDA receptor antagonist using a virtual screening approach," Bioorganic & Medicinal Chemistry Letters 20(2010) 5552-5558.
Ardayfio et al., J. Pharm and Exp Ther, 327:891-897, 2008.
Gaisler-Salomon et al., Psychopharm 196:255-267, 2008.
Carlsson et al., J. Neuraltrans. 106:123-129, 1999.
De Paulis, Curr Opin in Invest Drugs 2:123-132, 2001.

* cited by examiner

*Primary Examiner* — Jared D Barsky
(74) *Attorney, Agent, or Firm* — JMB Davis Ben-David

(57) ABSTRACT

Compositions and methods for the treatment of depression and psychoses in humans are disclosed. More particularly, the invention is directed to formulations containing antipsychotic and/or antidepressant medications and also containing an NMDAR antagonist. The present Invention Is also directed to methods tor the treatment of humans suffering from depression and other psychoses, including, schizophrenia, by administration of the inventive compositions in antidepressant and/or antipsychotic effective amounts.

6 Claims, 1 Drawing Sheet

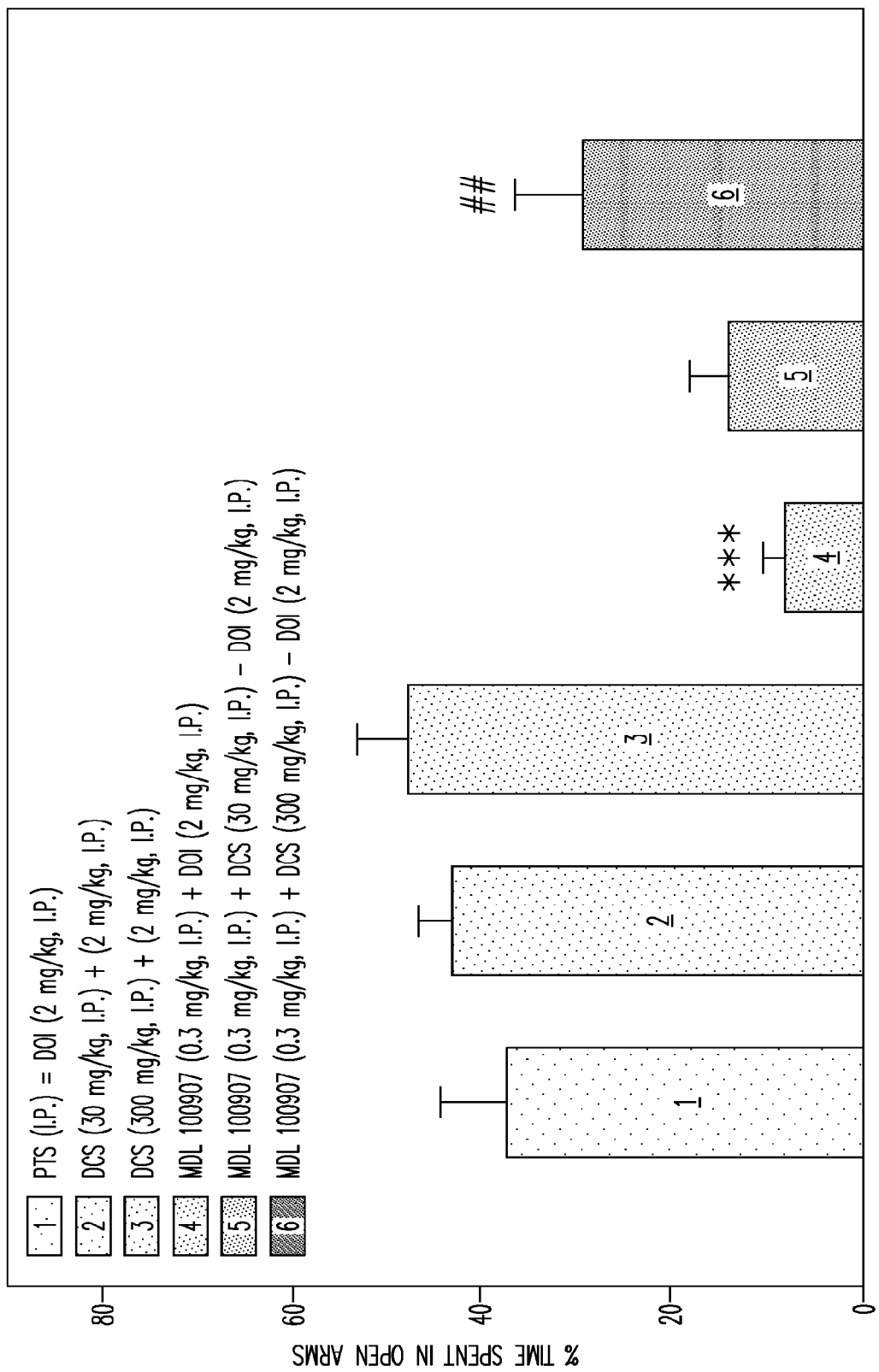

COMPOSITION AND METHOD FOR TREATMENT OF DEPRESSION AND PSYCHOSIS IN HUMANS

CROSS REFERENCE TO RELATED APPLICATIONS

This is a divisional of co-pending U.S. patent application Ser. No. 13/936,198, filed Jul. 7, 2013, which claims the benefit of provisional application No. 61/741,114, filed Jul. 12, 2012, and provisional application No. 61/741,115, filed Jul. 12, 2012, the contents of each of which are hereby incorporated by reference.

BACKGROUND OF THE INVENTION

Schizophrenia is a clinical syndrome associated with psychotic symptoms such as delusions and hallucinations, as well as a decline in function in such areas as work, social relation or self care.

Diagnosis of schizophrenia may be determined using standard textbooks of the art, such as the Diagnostic and Statistical Manual of Mental Disorders-fourth edition (DSM-IV) published by the American Psychiatric Association. Symptoms of schizophrenia are typically measured using rating scales such as the Positive and Negative Syndrome Scale (PANSS).

Symptoms of schizophrenia are treated with antipsychotic medications, which function primarily by blocking dopamine D2 receptors.

Antipsychotics may be divided into typical (e.g. chlorpromazine, haloperidol. perphenazine) vs. atypical (e.g. amisulpride, aripiprazole, asenapine, bioanserin, bifeprunox, cariprazine, clotiapine, clozapine, iloperidone, lurasidone, mosaproamine, olanzapine, paliperidone, perospirone, quetiapine, remoxipride, risperidone, sertindole, sulpiride, ziprasidone, zotepine) based upon receptor binding, preclinical effects and side effect profile. Clinically effective doses of antipsychotic medication typically produce >60% occupancy of dopamine D2 receptors. Atypical antipsychotics may be partial or full D2 antagonists and may also have activity at additional catecholamine and serotonin receptor types, including 5-HT2A and 5-HT2C receptors and adrenergic alpha1 and alpha2 receptors. Atypical antipsychotics may also affect other receptor types, such as such as muscarinic cholinergic receptors.

Major depression is a clinical syndrome that includes a persistent sad mood or loss of interest in activities, which persists for at least two weeks in the absence of treatment. Symptoms of major depression are typically measured using rating scales such as the Hamilton Depression Rating Scale (HAM-D) or the Beck Depression inventory (BDI). In addition to including symptoms relevant to depressed mood, the HAM-D also contains symptoms sensitive to psychosis, including items for guilt, depersonalization/derealization and paranoia. Major depression may also be associated with symptoms of anxiety, which may be measured with rating scales such as the Hamilton Rating Scale for Anxiety (HAM-A). Depressive disorders are divided in major depression (MDD) and bipolar depression (BPD), which may be diagnosed using criteria set forth in the Diagnostic and Statistical Manual, 4th edition, published by the American Psychiatric Association (DSM-IV), which provides as well additional description of mental disorders. Major depression may also occur with and without melancholic features. In addition, depressive symptoms may occur in the context of anxiety disorders such as generalized anxiety disorder, dissociative disorders, personality disorders or adjustment disorders with depressed mood (DSM-IV).

Current treatments for major depression consist primarily of older antidepressants, such as monoamine oxidase inhibitors (MAOI) and tricyclic antidepressants (TCAs) (e.g. imipramine, amitryptiline, desipramine, clomipramine) that were first developed in the 1960's, and newer agents such as tetracyclic antidepressants (TeCAs), e.g. amoxapine, setiptiline, maprotiline, mianserin, mirtazapine), serotonin (SSRI) and serotonin/norephinephrine (SNRI) reuptake inhibitors (e.g., fluoxetine, fluvoxamine, paroxetine, citalopram, escitalopram, duloxetine, venlafaxine, dapoxetine, indalpine, valzodone). These agents work by modulating brain levels of monoamines, in particular norepinephrine and serotonin, and/or by blocking 5-HT2A receptors. MAOIs and TCAs are considered "broader spectrum" agents than SSRIs/SNRIs that were developed subsequently MAOI, TCAs, TeCAs, SSRIs, and SNRIs may collectively be considered traditional antidepressants.

Antipsychotics may also be effective in treatment of depression. Potentially beneficial antipsychotic medications include but are not limited to risperidone, olanzapine, quetiapine, aripiprazole, clozapine, iloperidone, sertindole, asenapine, lurasidone, cariprazine.

Other antipsychotics and antidepressants in development include Valdoxan (agomelatine, AG0178) (Servier, Novartis), Lu AA21004 (Lundbeck, Takeda), F2695, levomilnacipran (Forest, Pierre Fabre), SEP-227162 (Sepracor), LuAA24530 (Lundbeck, Takeda). SEP-225289 (Sepracor), Epivanserine (Sanofi-Aventis), SR463 9 (Sanofi-Aventis). LY12624803, HY10275 (Lilly, Hypnion), TI-301/LY156735 (Tikvah Therapeutics), Lonasen (bioanserin, Dainippon), LU-31-130 (Lundbeck), SLV313 (Solvay). Edivoxetine (LY2216684, Lilly), OPC-34712 (Otsuka/Lundbeck), Vyvanse (lisdexamfetamine, Shire), BCI-224 (sacomeline, BrainCells), BCI-540 (clouracetam, BrainCells), BMS-82036 (BMS/AMRI).

However, current treatment approaches have severe limitations. Only 60-65% of patients respond to the initial regimen and among those responding, less than half either reach remission or become symptom-free. Individuals not responding to a first course of antidepressant treatment are often switched to a different drug, with results that are generally modest and incremental.

5-HT2A receptors are a type of receptor for the neurotransmitter serotonin. 5-HT2A antagonists are compounds that inhibit effects of agonists such as serotonin on 5-HT2A receptors. Inverse agonists are compounds that, in addition, reduce activity below basal levels. 5-HT2A receptor antagonists can be non-selective for 5-HT2A vs. other serotonin receptors (e.g. 5-HT2C), or selective for 5-HT2A receptors. Selective 5-HT2A antagonists can be developed and characterized using standard assay procedures, such as those described in U.S. Pat. No. 7,713,995 issued on May 11, 2010, which is herein incorporated by reference in its entirety.

Agents that act as non-selective serotonin receptor antagonists include ritanserin. ketanserin, seganserin, and ICI-169369. Agents that act as selective 5-HT2A antagonists or inverse agonists include volinanserin (MDL100.907, also known as M100907), pruvanserin (EMD281014), eplivanserin, CYR-101 and pimavanserin (ACP-103). Selective 5-HT2A receptor antagonists and inverse agonists are presently under development for treatment of both depression and psychosis and are viewed as potential antidepressant/antipsychotic agents.

Additional 5-HT2A receptor antagonists or inverse agonists are described in U.S. Pat. No. 7,875,632 which was issued on Jan. 25, 2011; U.S. Pat. No. 7,868,176 issued on Jan. 11, 2011; U.S. Pat. No. 7,863,296 issued on Jan. 4, 2011; U.S. Pat. No. 7,820,695 issued Oct. 26, 2010; and/or U.S. Pat. No. 7,713,995 issued May 11, 2010 which are herein incorporated by reference in its entirety.

Treatment-refractory depression refers to a form of depression that responds poorly to currently available treatments (e g, http://www.nimh.nih.gov/trials/practical/stard/index.shtml June 2011) and which may have different underlying etiopathological mechanisms compared with other forms of depression. Combinations of antidepressants have not been shown to be superior to monotherapy for refractory depression and typically increase risk of side effects and are not recommended.

Risk for suicide is significantly increased in depressive disorders, but may respond differentially to medication versus depressive symptoms as a whole. When suicide occurs, it is often accompanied by feelings of worthlessness or inappropriate guilt, as well as recurrent thoughts of death or suicidal ideation and guilt is an accepted proxy for suicide. While the risk of suicide increases in subjects with a depressive disorder, medications used to date to typically treat depressive disorders paradoxically increase suicidal tendencies.

A major limitation in use of antipsychotic and antidepressant medications is the liability to produce behavioral side effects, especially anxiety, agitation, and akathisia. These can be differentiated from symptoms of the illness by consideration of both time course and specific patterns of symptoms.

In addition to akathisia, antipsychotics also produce extrapyramidal symptoms such as stiffness, tremor or dyskinesia. Akathisia, however, is differentiated from extrapyramidal symptoms and shows differential treatment response. At present, there are no approved treatments for antipsychotic-induced akathisia.

Use of antidepressants is also limited by liability to produce anxiety, agitation, and akathisia.

Limitations of antidepressants are summarized in a "black box" warning required by the FDA, as follows: The following symptoms, anxiety, agitation, panic attacks, insomnia, irritability, hostility, aggressiveness, impulsivity, akathisia (psychomotor restlessness), hypomania, and mania have been reported in adult and pediatric patients being treated with antidepressants for major depressive disorder as well as for other indications, both psychiatric and non-psychiatric. Although a causal link between the emergence of such symptoms and either the worsening of depression and/or the emergence of suicidal impulses has not been established, there is concern that such symptoms may represent precursors to emerging suicidality" (Trivedi et al., J Olin Psychiatry. 72.765-774. 2011).

As with antipsychotic-induced akathisia, there are at present no known treatments for antidepressant induced anxiety, agitation, or akathisia.

Anxiety and akathisia may be studied in animal models, such as the rat defection or restlessness models, as described, for example, in Schdev & Brune, Animal models of acute drug-induced akathisia—a review. Neurosci Biobehav Rev 24:269-277. 2000).

Antipsychotics and antidepressants, including 5-HT2A receptor antagonists, may also be used therapeutically in the treatment of bipolar disorder (manic depressive psychosis), Alzheimers disease, Parkinsons disease, dementia, anxiety disorders, pain and developmental disorders including autism.

N-methyl-D-aspartate receptors (NMDAR) are a type of receptor for the brain neurotransmitter glutamate. NMDAR participate in a range of brain functions including sensory processing, cognition, and emotion regulation.

NMDAR are comprised of multiple subunits termed GluN1, GluN2 and GluN3 (formerly NR1, NR2, NR3). Multiple forms of GluN1, GluN2 and GluN3 exist. In particular, GluN2 subunits are divided into GluN2A-D subforms, which are also termed NR2A-D subunits. NMDAR may consist of various combinations of GluN1, GluN2 and GluN3 subunits in various amounts. Agonists and antagonists may affect all NMDAR equivalently, or may be selective for NMDAR containing specific subunit types.

NMDAR contain binding sites for both the neurotransmitter glutamate and for the endogenous modulatory amino acids glycine and D-serine.

The glutamate binding site also selectively binds the synthetic glutamate derivative N-methyl-D-aspartate with high affinity. This site is alternately referred to as the glutamate recognition site of the NMDA recognition site of the NMDAR.

The glycine/D-serine binding site has been referred to as the glycine modulatory site, the allosteric modulatory site or the glycine-B receptor.

NMDAR form an ion channel that is blocked by several drugs of abuse, such as phencyclidine (PCP), ketamine or dizocilpine (MK-801). These compounds bind to a site that has been termed the PCP receptor. Agents that block the NMDAR-associated ion channel are collectively termed noncompetitive NMDAR antagonists, or NMDAR channel blockers. Blockade of NMDAR by channel blockers leads to a clinical psychotic state that closely resembles schizophrenia.

Other compounds that block NMDA receptors via the channel site include AZD6765 (AstraZeneca) and Glyx-13 (Naurex). NRX-1059 (Naurex)

Other NMDAR antagonists are described in U.S. Patent appl. #20110306586 published Dec. 15. 2011, which is herein incorporated by reference in its entirety.

Low affinity NMDAR antagonists, such as memantine, may be distinguished from high affinity antagonists such as PCP, ketamine or dizocilpine. In general, low affinity NMDAR antagonists do not induce schizophrenia-like psychosis or PCP-like behavioral effects in rodents.

NMDAR may also be inhibited by antagonists that bind to the glutamate recognition sites, the glycine recognition site, or the channel binding site.

Selfotel (CGS19755) is an example of an antagonist that binds to the glutamate recognition site. Several such compounds were developed for CNS indications such as stroke or epilepsy. When used at doses sufficient to significantly inhibit NMDAR, these compounds, like channel blockers, lead to clinical psychotomimetic symptoms.

Additional compounds that functions as antagonists of the glutamate recognition site include aptiganel (Cerestat, CNS-1102) and related compounds as described in Reddy et al., J Med Chem 37:260-7. 1994.

Additional compounds that function as antagonists of the glutamate recognition site include alpha.-amino-carboxylic acid and phosphonic acid functionalities separated by a variety of spacer units. An unembellished example is 2-amino-5-phosphonovaleric acid (AP5) (Watkins, J. C; Evans, R. H., Annu. Rev. Pharmacol. Toxicol. 1981, 21, 165), which contains a saturated carbon chain. More complex examples, which contain elements enhancing structural rigidity and therefore potency, include CPP, cis-4-(phosphonomethyl)-2-piperidinecarboxylic acid (CGS-19755) (Lehman, J. et al., J. Pharmacol. Exp. Ther. 1988, 246, 65), and (E)-2-amino-4-methyl-5-phosphono-3-pentenoic acid (CGP-37849) (Schmutz, M. et al., Abs. Soc. Neurosci. 1988, 14. 864). See U.S. Pat. No. 7,345,032, issued Mar. 18, 2008 and U.S. Pat. No. 5,168,103, incorporated herein by reference in its entirety.

NMDAR may also be inhibited by antagonists that bind to the glycine recognition site.

D-cycloserine is a compound that acts as a partial glycine-site antagonist. D-cycloserine doses may be divided into low doses (0-250 mg), moderate (≥250-500 mg) or high (≥500 mg). At low dose, D-cycloserine may function as a net NMDAR agonist. At high doses, D-cycloserine may function as a net NMDAR antagonist. Plasma concentrations associated with moderate or high dose administration are >25 microgram/ml.

Felbamate is another example of a compound that may act via the glycine binding site. When administered to humans, felbamate produces psychotic effects that limit its clinical utility (e.g. Besag F M, Expert Opin Drug Saf 3:1-8, 2004).

Gavestinel (GV-150,526) is another example of a glycine binding site antagonist. Other compounds are described in DiFabrio et al., J Med Chem 40:841-50, 1997. which is hereby incorporated by reference.

Other examples of glycine site antagonists that are suitable for use in the pharmaceutical compositions and methods of this invention are those referred to in the following: U.S. Pat. No. 6,667,317 which was issued on Dec. 23, 2003; U.S. Pat. No. 6,080,743 which was issued Jun. 27, 2000; U.S. Pat. No. 5,990,108, which was issued on Nov. 23, 1999; U.S. Pat. No. 5,942,540, which issued on Aug. 24, 1999; World Patent Application WO 99/34790 which issued on Jul. 15. 1999; WO 98/47878, which was published on Oct. 29, 1998; World Patent Application WO 98/42673, which was published on Oct. 1. 1998; European Patent Application EP 966475A1, which was published on Dec. 29, 1991; World Patent Application 98/39327, which was published on Sep. 11, 1998; World Patent Application WO 98/04556, which was published on Feb. 5, 1998; World Patent Application WO 97/37652, which was published on Oct. 16. 1997; U.S. Pat. No. 5,837,705, which was issued on Oct. 9, 1996; World Patent Application WO 97/20553, which was published on Jun. 12, 1997; U.S. Pat. No. 5,886,018, which was issued on Mar. 23, 1999; U.S. Pat. No. 5,801,183. which was issued on Sep. 1, 1998, World Patent Application WO 95/07887, which was issued on Mar. 23, 1995; U.S. Pat. No. 5,686,461, which was issued on Nov. 11, 1997; U.S. Pat. No. 5,622,952, issued Apr. 22, 1997; U.S. Pat. No. 5,614,509, which was issued on Mar. 25, 1997; U.S. Pat. No. 5,510,367, which was issued on Apr. 23, 1996; European Patent Application 517.347A1, which was published on Dec. 9. 1992; U.S. Pat. No. 5,260,324, which published on Nov. 9. 1993. The foregoing patents and patent applications are incorporated herein by reference in their entireties.

Other examples of glycine site antagonists that can be used in the pharmaceutical composition and methods of this invention are N-{6,7-dichloro-2,3-dioxo-1,2,3,4-tetrahydro-quinoxalin-5-yl)-N-(2-hydroxy-ethyl)-methanesulfonamide and 6,7-dichloro-5-[3-methoxymethyl-5-(1-oxypyridin-3-yl)-[1,2,4]triazol-4-yl]-1,4-dihydro-quinoxa-line-2,3-dione.

Additional NMDAR antagonists are described in Schiene et al., U.S. Pat. Appl. No. US2001/0306674 A1, which is incorporated herein by reference in its entirety, and include without being limited thereto, N-containing phosphonic acids, such as norvaline (AP5), D-norvaline (D-AP5), 4-(3-phosphono-propyl)-piperazine-2-carboxylic acid (CPP), D-(E)-4-(3-phosphonoprop-2-enyl)piperazine-2-carboxylic acid (D-CPPene), cis-4-(phosponometyl)-2-piperidine carboxylic acid (Selfotel, CGS 19755), SDZ-220581, PD-134705, LY-274614 and WAY-126090; quinolinic acids, such as kynurenic acid, 7-chloro-kynurenic acid, 7-chloro-thiokynurenic acid and 57-dichloro-kynurenic acid, prodrugs thereof, such as 4-chlorokynurenine and 3-hydroxy-kynurenine; 4-aminotetrahydrochinolin-carboxylates, such as L-689,560; 4-hydroxyquinolin-2(1H)-ones, such as L-701,324; quinoxalinediones. such as Itcostinel (ACEA-1021) and CGP-68.730A; 4,6-dichloro-indole-2-carboxylate derivatives such as MDL-105,519, gavestinel (GV-150.526) and GV-196.771A; tricyclic compounds, such as ZD-9,379 and MRZ-2/576, (+)-HA-966, morphinan derivatives such as dextromethorphan and dextrophan; benzomorphans, such as BIII-277CL; other opioids, such as dextropropoxyphene, ketobemidone, dextromethadone and D-morphine; amino-adamantanes, such as amantadine and memantine; amino-alkyl-cyclohexanes, such as MRZ-2 579; ifenprodil and ifenprodile-like compounds such as eliprodil and PD-196, 860; iminopyrimidines; or other NMDA-antagonists such as nitroprusside, D-cycloserine. 1-aminocyclopropane-carbox-ylic acid, dizocilpine (MK 801) and its analogs, phencyclidine (PCP), ketamine ((R.S)-2-(2-Chlorphenyl)-2-(methyl-amino)cyclohexan-1-on), (R)-ketamine, (S)-ketamine, remacemide and its des-glycinyl-metabolite FPL-12.495, AR-R-15,896, methadone, sulfazocine, A 19/AVex-144, AN2/AVex-73, Besonprodil, CGX-1007, EAB-318. Felbamate and NPS-1407. N DA-Antagonists are, for example, disclosed in "Analgesics," edited by H. Buscmann, T. Christoph, E. Friderichs, C. Maul, B. Sundermann, 2002, Wiley-VCH Verlag GmbH & Co. KGaA, Weinheim, Germany, in particular pages 389-428. The respective parts of the description are hereby incorporated by reference and form part of the present disclosure.

Antagonists may be selective for the GluN2B (NR2B) containing subtype. Examples of compounds that are selective for NR2B containing receptors include ifenprodil, traxoprodil (CP-101.606). besonprodil, Ro25-6981 MK-0657 and EVT-101.

Along with identified NMDAR antagonists, additional can be identified using well-validated electrophysiological assays such as modulation of NMDA-receptor mediated responses to NMDA glutamate-site agonists, or radioreceptor assays, such as modulation of binding to the NMDA PCP-receptor channel binding site. Glycine site agonists and antagonists can also be distinguished based upon both electrophysiology and receptor binding from compounds such as phencyclidine (PCP) or ketamine that bind to the channel site. Partial agonists are defined as compounds that have reduced efficacy for inducing conformational change in receptors (typically 40-80%) relative to full agonists, and which may induce agonist effects at low dose but antagonist effects at high dose.

The NMDAR antagonist ketamine is currently approved as an anesthetic agent. It has also been reported to show beneficial effects in treatment resistant depression in small scale clinical trials. However, its utility is limited by psychotomimetic effects. The low affinity NMDAR antagonist memantine is approved for use in dementia. Otherwise, NMDAR antagonists have no established clinical utility.

In general, NMDAR antagonists are considered contraindicated for use in schizophrenia or depression. For example, the NMDAR antagonist D-cycloserine is contraindicated by FDA for use in depression, severe anxiety or psychosis.

Here we show unexpectedly that NMDAR antagonists unexpectedly reduce akathisia and anxiety associated with antidepressant and/or antipsychotic treatment.

Here we show unexpectedly that antidepressants prevent psychotic symptoms associated with NMDAR agonist usage.

These findings provide a method for improved treatment of humans requiring treatment with an antipsychotic, antidepressant, or NMDAR antagonist medication.

BRIEF DESCRIPTION OF THE DRAWING

FIG. 1 is a graphical representation of the results described in the Example described hereinafter showing the percent of time spent in the open arms of the testing device for very drugs or combination of drugs.

SUMMARY OF THE INVENTION

The present invention is directed towards compositions for the treatment of depression and psychoses in humans. More particularly, the invention is directed to formulations containing antipsychotic and or antidepressant medications including selective 5-HT2A receptor antagonists/inverse agonists and also containing an NMDAR antagonist. The present invention is also directed to methods for the treatment of humans suffering from depression and other psychoses, including, schizophrenia, by administration of the inventive compositions in antidepression and/or antipsychotic effective amounts.

In one embodiment, this invention provides an oral or parenteral dosage regimen consisting essentially of two therapeutic agents, wherein a first of said two active ingredients is an antidepressant or antipsychotic agent, and the second agent consists of an NMDAR receptor antagonist.

In some embodiments of the invention, the first compound consists of a typical or atypical antipsychotic agent In some embodiments of the invention, the first therapeutic agent is drawn from a list that includes amisulpride, aripiprazole, asenapine, bifeprunox, bioanserin, cariprazine, clotiapine, clozapine, iloperidone, lurasidone, mosaproamine, olanzapine, palipendone, perospirone, quetiapine, remoxi pride, risperidone, sertindole, sulpiride, ziprasidone, zotepine.

In some embodiments, the first therapeutic agent comprises a tetracyclic antidepressant (TeCA), selective serotonin reuptake inhibitor (SSRI), a serotonin/norephinephrine reuptake inhibitor (SNRI)a 5-HT2A antagonist/inverse agonist or a combination thereof.

5-HT2A receptor antagonists/inverse agonists may be drawn from a list that includes volinanserin (MDL 100.907, also known as M100907) pruvanserin (EMD281014), eplivanserin, CYR-101 and pimavanserin (ACP-103).

NMDAR antagonists may be drawn from antagonists at the glycine, glutamate or channel recognition sites.

NMDAR antagonists may be non-selective antagonists or selective antagonists at NMDAR containing specific subunits such as the NR2A or NR2B subunits.

In some embodiments of the invention, the antidepressant may be selected from the group consisting of includes imipramine, amitryptiline, desipramine, clomipramine, amoxapine, setiptiline, maprotiline, mianserin, mirtazapine, fluoxetine, fluvoxamine, paroxetine, citalopram, escitalopram, duloxetine, venlafaxine. dapoxetine, indalpme, valzodone.

In some embodiments of the invention, the first therapeutic agent is drawn from a list that includes agomelatine, Lu AA21004, F2695, levomilnacipran, SEP-227162, LuAA24530, SEP-225289, Epivanserine, SR46349, LY12624803, HY10275, TIK-301/LY156735, Lonasen, LU-31-130. SLV313, Edivoxetine, OPC-34712, lisdexamfetamine, sacomeline, clouracetam, and BMS-82036.

In some embodiments, the second therapeutic agent is drawn from a list that includes ketamine, dextromethorphan, CNS-1 102.AZD6765 or CGS-19755.

In a preferred embodiment of the invention, the second therapeutic agent consists of D-cycloserine, administered at a dosage of at least 500 mg per day.

In some embodiments, the NMDA receptor antagonists consists of D-cycloserine, administered at a dose that produces serum levels in excess of 25 microgram/mL.

In some embodiments, this invention provides a method for treatment of a psychosis in a subject in need thereof, said method comprising providing said subject with an oral or parenteral dosage regimen as herein described.

In some embodiments, this invention provides a method for treatment of depression in a subject in need thereof, said method comprising providing said subject with an oral or parenteral dosage regimen as herein described.

In some embodiments, the subject suffers from mania, or in some embodiments, the subject suffers from bipolar disorder.

In some embodiments, this invention provides a method for treating symptoms of autism in a subject in need thereof, said method comprising providing said subject with an oral or parenteral dosage regimen as herein described.

In some embodiments, the invention provides a method for reducing side effects associated with antipsychotic medications to a subject in need of such treatment, said method comprising providing said subject with an oral or parenteral dosage regimen as herein described.

In some embodiments, this invention provides a method for reducing side effects associated with antidepressant medications to a subject in need of such treatment, said method comprising providing said subject with an oral or parenteral dosage regimen as herein described.

In some embodiments, this invention provides a method for reducing side effects associated with NMDAR antagonist medications to a subject in need of such treatment, said method comprising providing said subject with an oral or parenteral dosage regimen as herein described.

In some embodiments, a gelling agent such as hydroxypropyl methylcellulose, together with one or more pharmaceutically acceptable excipients is used for manufacture of the sustained release agent.

In some embodiments, the sustained release formulation comprises a hydrophilic matrix comprising a gelling agent, preferably hydroxypropyl methylcellulose, an NMDA receptor antagonist, an antidepressant and pharmaceutically acceptable salts thereof, together with one or more pharmaceutically acceptable excipients.

In some embodiments both the NMDA receptor antagonist and the antidepressant or antipsychotic medication would be manufactured for sustained release in common.

In some embodiments, the NMDA receptor antagonist would be manufactured for sustained release, and combined with an antidepressant or antipsychotic agent.

In some embodiments, the antidepressant or antipsychotic agent would be manufactured for sustained release, and combined with an NMDA receptor antagonist.

In one embodiment, an NMDA receptor antagonist and an antidepressant or antipsychotic agent would be selected for release characteristics permitting once daily dosing of the combined medicament, and would not require separate sustained release manufacture.

DETAILED DESCRIPTION OF THE INVENTION

This invention provides, in some embodiments, parenteral or intravenous dosage regimens, which are useful in the treatment of schizophrenia or depression in a subject in need thereof, or in the reduction of the incidence or akathisia or anxiety in a subject or population in need thereof.

In some embodiments, the invention provides an oral or parenteral dosage regimen consisting essentially of two active ingredients, wherein a first of said ingredients is an antipsychotic or antidepressant agent.

In some embodiments, according to this aspect, the first therapeutic agent comprises any such agent as herein described, for example, a tetracyclic antidepressant (TeCA), selective serotonin reuptake inhibitor (SSRI), a serotonin/ norephinephrine reuptake inhibitor (SNRI), a selective 5-HT2A receptor antagonist, a selective 5-HT2A receptor inverse agonist, an antipsychotic approved for use in treatment of depression or a combination thereof.

In some embodiments, the selective 5-HT2A antagonist/ inverse agonist is selected from the group consisting of volinanserin (MDL100.907, M100907) pruvanserin (EMD281014), eplivanserin, CYR-101 and pimavanserin (ACP-103).

In some embodiments, the first therapeutic agent is an antipsychotic agent, consisting of a typical or atypical antipsychotic.

In some embodiments, the antipsychotic agent is selected from the group consisting of amisulpride, aripiprazole, asenapine, bioanserin, bifeprunox, cariprazine, clozapine, clozapine, iloperidone, lurasidone, mosaproamine, olanzapine, paliperidone, perospirone, quetiapine, remoxi pride, risperidone, sertindole, sulpiride, ziprasidone, zotepine.

In some embodiments, the second therapeutic agent is an NMDAR antagonist.

In some embodiments, the second therapeutic agent acts at the glycine, glutamate or channel recognition sites.

In some embodiments, the second therapeutic agent acts at NMDAR containing NR2A subunits.

In some embodiments, the second therapeutic agent acts at NMDAR containing NR2B subunits.

In some embodiments, the second therapeutic agent is drawn from a list that includes ketamine, Selfotel, aptiganel, CPP, CGP-37849, felbamate, Gavestinel N-(6,7-dichloro-2, 3-dioxo-1,2,3,4-tetrahydro-quinoxalin-5-yl)-N-(2-hydroxyethyl)-methanesulfonamide and 6,7-dichloro-5-[3-methoxymethyl-5-(1-oxypyridin-3-yl)-[1,2.4]triazol-4-yl]-1,4-dihydro-quinoxa-line-2,3-dione, 4-(3-phosphonopropyl)-piperazine-2-carboxylic acid (CPP), D-(E)-4-(3-phosphonoprop-2-enyl)piperazine-2-carboxylic acid (D-CPPene), SDZ-220581, PD-134705.LY-274614 and WAY-126090; quinolinic acids, such as kynurenic acid, 7-chloro-kynurenic acid, 7-chloro-thiokynurenic acid and 5,7-dichloro-kynurenic acid, prodrugs thereof, such as 4-chlorokynurenine and 3-hydroxy-kynurenine; 4-aminotetrahydrochinolin-carboxylates, such as L-689.5604-hydroxyquinolin-2(1H)-ones, such as L-701,324; quinoxalinediones, such as licostinel (ACEA-1021) and CGP-68.730A; 4,6-dichloro-indole-2-carboxylate derivatives such as MDL-105,519, gavestinel (GV-150,526) and GV-196.771A; tricyclic compounds, such as ZD-9,379 and MRZ-2/576, (+)-HA-966, morphinan derivatives such as dextromethorphan and dextrophan; benzomohans, such as BIII-277CL; other opioids, such as dextropropoxyphene, ketobemidone, dextromethadone and D-morphine; amino-adamantanes, such as amantadine and memantine; amino-alkyl-cyclohexanes, such as MRZ-2579; ifenprodil and ifenprodile-li e compounds such as eliprodil and PD-196,860; iminopyrimidines; or other NMDA-antagonists such as nitroprusside, D-cycloserine, 1-aminocyclopropane-carboxylic acid, dizocilpine (MK 801) and its analogs, (R)-ketamine, (S)-ketamine, remacemide and its des-glycinyl-metabolite FPL-12, 495, AR-R-15,896, methadone, sulfazocine, A 19/AVex-144, AN2/AVex-73, Besonprodil, CGX-1007.EAB-318, and NPS-1407.

In some embodiments, the second compound is D-cycloserine, administered at a dose of 500 mg or greater.

In some embodiments, the two active ingredients are provided in a single pharmaceutical composition, and in some embodiments, the invention contemplates a kit or combined dispenser packet containing each of the two active ingredients.

It is to be understood that the invention contemplates the co-administration of either of the two active ingredients to a subject, whether such administration is combined in a single formulation or in separate formulations and whether such administration is coincident or staggered.

The inventive composition may be administered by a variety of well-established medicinal routes including intravenously, intraperitoneally, parentally, intramuscularly, or orally.

In some embodiments, this invention provides a method for treating depression in a subject in need thereof, said method comprising administering an effective amount of the inventive composition in the form of an oral or parenteral dosage or a parenteral injection as herein described.

In some embodiments, the subject suffers from schizophrenia, or in some embodiments, the subject suffers from bipolar disorder. In some embodiments, the invention provides a method for reducing the incidence or treating suicide or suicide ideation in a subject or population in need thereof, the method comprising providing the subject with an oral or parenteral or parenteral dosage regimen as herein described.

In some embodiments, reference to an "effective" amount or a "therapeutically effective amount" of therapeutic agents referenced herein, it is meant a nontoxic but sufficient amount of the same to provide the desired effect. In a combination therapy of the present invention, an "effective amount" of one component of the combination is the amount of that compound that is effective to provide the desired effect when used in combination with the other components of the combination. The amount that is "effective" will vary from subject to subject, depending on the age and general condition of the individual, the particular active agent or agents, and the like. Thus, it is not always possible to specify an exact "effective amount" However, an appropriate "effective" amount in any individual case may be determined by one of ordinary skill in the art using routine experimentation The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual.

D-cycloserine, or DOS, refers to the chemical D-cycloserine (CA Index Name.3-Isoxazolidinone, 4-amino-, (4R)-

(9Cl); CAS Registry No. 68-41-7), or pharmaceutically acceptable salts thereof. DCS is an FDA (United States Food and Drug Administration)-approved drug for treatment of tuberculosis, and is sold by Eli Lilly and Company under the trade name Seromycin®DCS is a structural analog of D-alanine, and is a broad-spectrum antibiotic produced by some strains of *Streptomyces orchidaceus* and *S. garphalus*. In some embodiments, the inventive combination may be used in the treatment of tuberculosis.

Indicia is provided and disposed adjacent the columns and rows for displaying common days and successive weeks. Thus, the package provides for a titration schedule which prevents adverse events as a result of mis-dosing. As a result, the package in accordance with the present invention provides for a safer and accordingly more beneficial method for enabling compliance with the regimen.

In some embodiments, according to this aspect, the first therapeutic agent is administered at a dosage, which is considered to be suboptimal for treating depression or psychosis in said subject when treating said subject with said first therapeutic agent alone.

A subject undergoing treatment with the methods of the invention can experience significant improvements in depression. Relative to subjects treated with alternative treatments for depression, subjects treated according to the methods of the invention will experience, in some embodiments, greater improvement, or more long-lasting improvement, as measured by any clinically recognized assessment method for depression (e.g., the 21-item Hamilton Depression Rating Scale). It should be noted that not every subject will benefit from the methods of the invention, just as other pharmaceutical agents do not typically benefit every patient.

A subject undergoing treatment with the methods of the invention can experience significant improvements in anxiety. Relative to subjects treated with alternative treatments for anxiety, subjects treated according to the methods of the invention will experience, in some embodiments, greater improvement, or more long-lasting improvement, as measured by any clinically recognized assessment method for anxiety (e.g., the Hamilton Anxiety Rating Scale). It should be noted that not every subject will benefit from the methods of the invention, just as other pharmaceutical agents do not typically benefit every patient A subject undergoing treatment with the methods of the invention can experience significant improvements in akathisia. Relative to subjects treated with alternative treatments for akathisia, subjects treated according to the methods of the invention will experience, in some embodiments, greater improvement, or more long-lasting improvement, as measured by any clinically recognized assessment method for akathisia (e.g, the Barnes Akathisia Rating Scale). It should be noted that not every subject will benefit from the methods of the invention, just as other pharmaceutical agents do not typically benefit every patient.

A subject undergoing treatment with the methods of the invention can experience significant improvements in psychosis. Relative to subjects treated with alternative treatments for psychosis, subjects treated according to the methods of the invention will experience, in some embodiments, greater improvement, or more long-lasting improvement, as measured by any clinically recognized assessment method for psychosis (e.g., the Positive and Negative Symptom Scale). It should be noted that not every subject will benefit from the methods of the invention, just as other pharmaceutical agents do not typically benefit every patient.

EXAMPLE

Example

Effect of NMDAR Antagonists on Akathisia Induced by 5-HT2A Antagonists

Background: Drug induced akathisia is a common side effects of both antipsychotic and antidepressant medication and may be seen even with newer atypical antipsychotics (Iqbal et al., CNS Spectrums, 12:1-13, 2007). This syndrome has also been described as anxiety/jitteriness syndrome (Sinclair et al., Br J Psychiatry, 194:483-90, 2009), which is also seen following both SSRIs and tricyclic antidepressants.

Although no exact animal models exist at present, rodent activity measures which asses partial restlessness have been proposed to have face validity (Sachdev and Brune. Neurosci Biobehav Rd 24:269-277, 2000), justifying their use. Agonists at the 5-HT2A receptor, such as (+/−)-1-(2,5-dimethoxy-4-iodophenyl)-2-aminopropane (DOI) have well described anxiolytic properties that may be detected in rodent assays such as the four-plate test or the elevated plus maze (Nic Dhonnchadha et al Behavioural brain research. 147:175-84, 2003). Effects of 5-HT2A ligands may be mediated in part via the GABA system (Masse et al., Behav Brain Res 177:214-26. 2007), increasing the relevance of this mechanisms for akathisia The present investigation tests the hypothesis that NMDA receptor antagonists may reverse the akathasia-induced effects of agents that work in whole or in part through 5-HT2A blockade, including selective 5-HT2A antagonists/inverse agonists, anti-depressants, and atypical antipsychotics. For this study, the primary NMDA receptor antagonist used was D-cycloserine (DCS).

Methods: All studies were performed at PsychoGenics, Inc., headquartered at 765 Old Saw Mill River Road, Tarrytown, N.Y. using an elevated plus maze (EPM) apparatus to assess behavioral effects of medication.

Preparation: Male C57Bl/6J mice from Jackson Laboratories (Bar Harbor, Me.) were used for this study. Mice were received at 6-weeks of age. Upon receipt, mice were assigned unique identification numbers (tail marked) and were group housed with 4 mice/cage in OPTI mouse ventilated cages. All animals remained housed in groups of four during the remainder of the study. All mice were acclimated to the colony room for at least 1 week prior to testing and were subsequently tested at an average of 7 weeks of age During the period of acclimation, mice were examined on a regular basis, handled, and weighed to assure adequate health and suitability. Animals were maintained on a 12/12 light/dark cycle; testing was performed during the light phase. The room temperature was maintained between 20 and 23° C. with a relative humidity maintained between 30% and 70%. Chow and water were provided ad libitum for the duration of the study. In each test, animals were randomly assigned across treatment groups. All animals were euthanized after the completion of the study.

Apparatus: The elevated plus maze test assessed anxiety. The maze (Kinder Scientific; Poway, Calif.) consists of two closed arms (14.5 cm h×5 cm w×35 cm l) and two open arms (6 cm w×35 cm l) forming a cross, with a square center platform (6×6 cm). All visible surfaces are made of black acrylic. Each arm of the maze was placed on a support column 56 cm above the floor. Antistatic black vinyl curtains (7' high) surround the EPM to make a 5' w×5' l enclosure. Animals were allowed to acclimate to the experimental room at least 1 hr before the test. Mice were placed in the center of the elevated plus maze facing the closed arm for a 5-min run. All animals were tested once. The time spent, distance traveled, and entries in each arm were automatically recorded by the computer. The EPM was thoroughly cleaned after each test.

Medications: Medications were administered by ip injection. All medications were dissolved in appropriate vehicle. Doses are expressed in milligrams per kilogram (mpk).

Statistical analysis. The primary dependent measure for this study consisted of % of time spent within the open arms, which is considered a measure of anti-anxiety effects. Between-condition comparisons were performed using post-hoc LSD with one-tailed significance of p<05.

Results: Specific effects of NMDA receptor antagonists on anxiety/akathisia related symptoms were assessed using the measure % time in open arms, which measures willingness to enter an exposed vs. enclosed section of the EPM. Because it represents a ratio between activity in open and closed arms, it is relatively insensitive to changes in overall activity levels. Potential non-specific effects were assessed using the total distance traveled, which is a measure of overall activation. Locomotor hyperactivity induced by NMDA antagonists is considered a rodent model of psychosis. 5-HT2A antagonists are known to reverse effects of high-affinity NMDAR channel blockers on rodent activity, reflecting their potential use as anti-psychotics. However, no studies have previously investigated the ability of competitive NMDAR antagonists acting at either the glycine or glutamate sites to reverse potential akathisia-related anxiogenic effects of high affinity 5-HT2A antagonists, or other compounds such as anti-depressants or atypical antipsychotics potentially associated with antagonism at 5-HT2A receptors.

Description of the Results.

The results of the foregoing described experiments are set forth in Table 1. Results of an individual representative experiment are set forth in Table 2 and depicted in FIG. 1.

TABLE 1

| DOI Control | Dose DOI | 5-HT2A antagonist | Dose | NMDA antagonist | Dose | N | % time spent in open arm Mean | Std. Dev. | Distance travelled Mean | Std. Dev. |
|---|---|---|---|---|---|---|---|---|---|---|
| Control | 0 | — | | — | | 10 | 22.438 | 14.6418 | 786.30 | 68.531 |
| DOI | 1 mpk | — | | — | | 10 | 46.859 | 22.3661 | 687.10 | 108.721 |
| DOI | 2 mpk | — | | — | | 30 | 37.241 | 17.7516 | 678.20 | 96.958 |
| DOI/D-cycloserine | 2 mpk | — | | D-cycloserine | 30 mpk | 10 | 44.598 | 10.6373 | 781.50 | 96.345 |
| DOI/D-cycloserine | 2 mpk | — | | D-cycloserine | 300 mpk | 10 | 48.088 | 14.9833 | 733.70 | 76.202 |
| DOI (2 mpk)+ | | | | | | | | | | |
| MDL100907 | 1 | MDL100907 | 0.3 mpk | — | | 10 | 26.760 | 17.6137 | 693.20 | 69.089 |
| MDL100907 | 2 mpk | MDL100907 | 0.3 mpk | — | | 40 | 21.938 | 21.4108 | 741.70 | 85.718 |
| MDL100907/D-cycloserine | 2 mpk | MDL100907 | 0.3 mpk | D-cycloserine | 30 mpk | 10 | 20.807 | 24.1793 | 735.10 | 131.341 |
| MDL100907/D-cycloserine | 2 mpk | MDL100907 | 0.3 mpk | D-cycloserine | 300 mpk | 10 | 35.828 | 29.2316 | 887.10 | 105.288 |
| MDL100907/CGS19755 | 2 mpk | MDL100907 | 0.3 mpk | CGS-19755 | | 10 | 21.749 | 19.2252 | 527.00 | 139.276 |
| MDL100907/CPPene | 2 mpk | MDL100907 | 0.3 mpk | D-CPPene | | 10 | 31.813 | 22.6649 | 727.90 | 66.527 |
| MDL100907/CP101606 | 2 mpk | MDL100907 | 0.3 mpk | CP101606 | | 9 | 25.122 | 18.9580 | 775.00 | 157.463 |
| MDL100907/GV150526A | 2 mpk | MDL100907 | 0.3 mpk | GV150526A | | 11 | 20.818 | 16.6459 | 663.55 | 93.861 |
| MDL100907/L701324 | 2 mpk | MDL100907 | 0.3 mpk | L701324 | | 10 | 25.980 | 31.5739 | 522.90 | 169.097 |
| MDL100907/PCP | 2 mpk | MDL100907 | 0.3 mpk | PCP | 1 mpk | 10 | 14.916 | 13.6545 | 792.50 | 155.336 |
| Ketanserin | 2 mpk | Ketanserin | 2 mpk | — | | 10 | 10.400 | 11.0660 | 648.90 | 161.515 |
| Ketanserin/D-cycloserine | 2 mpk | Ketanserin | 2 mpk | D-cycloserine | 300 mpk | 10 | 21.390 | 18.2661 | 640.80 | 96.388 |
| EMD281014 | 2 mpk | EMD281014 | 30 mpk | — | | 10 | 23.050 | 20.7257 | 628.20 | 110.375 |
| EMD281014/D-cycloserine | 2 mpk | EMD281014 | 30 mpk | D-cycloserine | 300 mpk | 10 | 27.380 | 26.7496 | 541.10 | 148.073 |
| Antipsychotics | | | | | | | | | | |
| Lurasidone | 2 mpk | Lurasidone | 1 mpk | — | | 10 | 36.020 | 16.2589 | 715.50 | 116.712 |
| Lurasidone/D-cycloserine | 2 mpk | Lurasidone | 1 mpk | D-cycloserine | 300 mpk | 10 | 53.230 | 17.6298 | 739.10 | 91.594 |

TABLE 1-continued

| DOI Control | Dose DOI | 5-HT2A antagonist | Dose | NMDA antagonist | Dose | N | % time spent in open arm Mean | Std. Dev. | Distance travelled Mean | Std. Dev. |
|---|---|---|---|---|---|---|---|---|---|---|
| Quetiapine | 2 mpk | Quetiapine | 30 mpk | — |  | 10 | 8.950 | 10.6937 | 675.50 | 116.319 |
| Quetiapine/ D-cycloserine | 2 mpk | Quetiapine | 30 mpk | D-cycloserine | 300 mpk | 10 | 26.004 | 28.9504 | 630.20 | 140.271 |
| Antidepressants |  |  |  |  |  |  |  |  |  |  |
| Duloxetine | 2 mpk | Duloxetine | 10 mpk | D-cycloserine | 300 mpk | 10 | 22.290 | 30.4841 | 979.50 | 181.190 |
| Mirtazapine | 2 mpk | Mirtazapine | 5 mpk | D-cycloserine | 300 mpk | 10 | 25.282 | 22.3245 | 764.20 | 97.790 |
| Venlafaxine | 2 mpk | Venlafaxine | 16 mpk | D-cycloserine | 300 mpk | 10 | 21.144 | 12.0805 | 928.50 | 78.921 |

TABLE 2

| Bar No. | Condition | Mean | SEM | N |
|---|---|---|---|---|
| 1 | PTS-DOI (2 mg/kg) | 35.56903 | 6.428943 | 10 |
| 2 | DCS (30 mg/kg) – DOI (2 mg/kg) | 44.59816 | 3.363823 | 10 |
| 3 | DCS (300 mg/kg) – DOI (2 mg/kg) | 48.1 | 4.7 | 10 |
| 4 | MDL100907 (0.3 mg/kg) – DOI (2 mg/kg) | 9.553678 | 2.931169 | 10 |
| 5 | MDL100907 (0.3 mg/kg) + DCS (30 mg/kg) – DOI (2 mg/kg) | 20.8 | 7.6 | 10 |
| 6 | MDL100907 (0.3 mg/kg) + DCS (300 mg/kg) – DOI (2 mg/kg) | 35.8 | 9.2 | 10 |

DOI (2 mpk) significantly increased % time spent in open arms saline at doses of both 1 mpk ($p<0.05$) and 2 mg ($p<0.05$) DCS had no significant effect when added to DOI alone at doses of either 30 mpk or 300 mpk, suggesting absence of non-specific behavioral effects in this assay system. DCS (300 mpk) significantly reversed effects of MDL100709 ($p<0.05$), whereas effects of DCS (30 mpk) were non-significant. Furthermore, % time spent in open arms was numerically greater for combined DCS (300 mpk) and both ketanserin and E D28101 than with either agent alone. When analyses were performed within experiment, a highly significant effect of D-cycloserine (300 mpk) vs. DOI (2 mpk) and MDL100,907 (0.3 mpk) alone was observed ($p<0.01$) (FIG. 1).

In the presence of DOI (2 mpk), both the 5-HT2A antagonists/inverse antagonists MDL100907 ($p=0.001$) and ketanserin ($p<0.001$) and EMD281014 ($p<0.05$) significantly reduced % time spent in open arms, suggesting a significant liability for akathisia.

The competitive glutamate site antagonist D-CPPene produced trend level reversal of effects of MDL100.907 ($p<0.1$) on % time spent in open arms. Other NMDA receptor antagonists, including CGS19755 and CP101606 produced numerical improvement. No significant effect was observed for the channel site antagonist POP, although the tendency was for exacerbation of effect. Furthermore, % time spent in open arms in the presence of combined D-cycloserine/DOI/ DL100907 was significantly greater than in the presence of combined PCP/DOI MDL100907 ($p<0.05$).

In addition to selective 5-HT2A antagonists/inverse agonists, the atypical antipsychotics quetiapine ($p<0.001$) and lurasidone ($p<0.05$) also significantly reduced % time in open arms, suggesting a liability to induce akathisia. For both quetiapine ($p<05$) and lurasidone ($p<0.05$) effects were significantly reversed by DOS 300 mpk.

Finally, three antidepressants—duloxetine, mirtazapine, and venlafaxine were tested in the presence of D-cycloserine (300 mpk) and DOI (2 mpk). All 3 showed significantly reduced % open arm entries vs. DOI alone, consistent with ability to induce akathisia clinically.

Distance Traveled (DT)

As opposed to % time in open arms. DOI (2 mpk) significantly reduced total distance traveled. MDL100907 significantly increased DT vs. DOI (2 mpk) alone ($p<0.05$), and this effect was enhanced (rather than reversed) by D-cycloserine (300 mpk) ($p<0.001$). Other 5-HT2A and NMDAR antagonists had inconsistent effects alone and in combination with pattern different for that observed for the % time spent in open arm measure, reflecting specificity of the anti-akathisia effects. As a group, duloxetine, venlafaxine and mirtazapine added to DOI (2 mpk) and D-cyclosrerine (300 mpk) significantly enhanced DT compared to DOI (2 mpk) and D-cycloserine (300 mpk) alone ($p<0.05$).

Summary

These findings demonstrate an unexpected ability of D-cycloserine, at high doses, to reverse reductions in % time spent in the open arm of the elevated plus maze induced by 5-HT2A antagonists such as MDL100709, ketanserin or atypical antipsychotics Pro-therapeutic effects were seen not only for D-cycloserine, but also for other NMDA receptor antagonists such as D-CPPene, CGS19755 or CP 101606. In contrast, the traditional channel blocker PCP worsened performance relative to DCS, suggesting that agents working at the glutamate or glycine binding sites, or lower affinity channel blockers, such as GlyX-13, may be superior to higher affinity non-competitive antagonists such as PCP or MK-O'I. Furthermore, although 5-HT2A antagonists are known to reverse hyperactivity induced by NMDA channel blockers such as ketamine, MK-801, or PCP, the % open arm measure (which compares distance traveled in open vs. closed arms) corrects for overall changes in activity levels.

Although the present animal models leave open the degree to which the phenomenon observed in rodents is isomorphic with drug-induced akathisia and/or jitteriness/ anxiety syndrome in humans, this issue is immaterial to the claimed invention, which nevertheless shows highly potent and unexpected reversal of anxiogenic properties of 5-HT2A antagonistic and atypical antipsychotic compounds by D-cycloserine and other NMDA receptor antagonists. These findings thus suggest a unique and unexpected benefit from the addition of NMDA receptor antagonists to 5-HT2A antagonists including typical/atypical antagonists and antidepressants, and suggests that undesirable anxiogenic side effects of these compounds can be minimized by the use of NMDAR antagonists.

While certain features of the invention have been illustrated and described herein, many modifications, substitutions, changes, and equivalents will now occur to those of ordinary skill in the art. It is therefore, to be understood that the appended claims are intended to cover all such modifications and changes as fall within the true spirit of the invention.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range unless otherwise specified. Furthermore, it is to be understood that unless otherwise indicated or otherwise evident from the context and understanding of one of ordinary skill in the art values that are expressed as ranges can assume any specific value or subrange within the stated ranges, optionally including or excluding either or both endpoints, in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

In the claims articles such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in. or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one or all of the group members are present in, employed in. or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

I claim:

1. A method for reducing akathisia caused by lurasidone treatment in a subject with bipolar disorder, comprising:
   administering an akathisia-inducing amount of lurasidone to the subject;
   once akathisia is induced, continuing to administer lurasidone at a same dosage and frequency that caused akathisia; and
   administering a therapeutically effective amount of a second composition comprising D-cycloserine (DCS) at a dosage in excess of 500 mg/day, wherein the DCS produces a NMDA receptor antagonistic blood plasma concentration measured at greater than 25 micrograms/mL,
   thereby reducing akathisia.

2. A method for reducing the incidence of akathisia caused by lurasidone treatment in a subject with bipolar disorder, comprising:
   administering therapeutically effective amounts of lurasidone, ketamine, and D-cycloserine (DCS) to a subject with bipolar disorder, wherein DCS is administered at a dosage in excess of 500 mg/day,
   wherein the DCS produces a NMDA receptor antagonistic blood plasma concentration measured at greater than 25 micrograms/mL, thereby reducing the incidence of akathisia caused by lurasidone.

3. The method of claim 1, wherein the lurasidone and second composition are administered intramuscularly, intravenously, intraperitoneally, parentally, or orally.

4. The method of claim 2, wherein the lurasidone, ketamine, and D-cycloserine (DCS) are administered intramuscularly, intravenously, intraperitoneally, parentally, or orally.

5. The method of claim 1, wherein the wherein the lurasidone and second composition are formulated as a single composition for administration to the subject.

6. The method of claim 2, wherein the wherein the lurasidone, ketamine, and D-cycloserine (DCS) are formulated as a single composition for administration to the subject.

* * * * *